(12) United States Patent
Saidman et al.

(10) Patent No.: US 10,729,319 B2
(45) Date of Patent: Aug. 4, 2020

(54) OPTHALMIC DEVICE FOR FUNDUS EXAMINATION

(71) Applicants: Gabriela Saidman, Berazategui Provincia de Buenos Aires (AR); Guillermo Andres Monteoliva, La Plata Provincia de Buenos Aires (AR)

(72) Inventors: Gabriela Saidman, Berazategui Provincia de Buenos Aires (AR); Guillermo Andres Monteoliva, La Plata Provincia de Buenos Aires (AR)

( * ) Notice: Subject to any disclaimer, the term of this patent is extended or adjusted under 35 U.S.C. 154(b) by 0 days.

(21) Appl. No.: 16/358,813

(22) Filed: Mar. 20, 2019

(65) Prior Publication Data
US 2019/0290116 A1    Sep. 26, 2019

(30) Foreign Application Priority Data
Mar. 20, 2018    (AR) .................... 180100639

(51) Int. Cl.
| | |
|---|---|
| *A61B 3/00* | (2006.01) |
| *A61B 17/02* | (2006.01) |
| *A61B 3/12* | (2006.01) |
| *A61B 5/00* | (2006.01) |
| *A61B 17/00* | (2006.01) |
| *A61B 90/30* | (2016.01) |

(52) U.S. Cl.
CPC .............. *A61B 3/0008* (2013.01); *A61B 3/12* (2013.01); *A61B 5/0053* (2013.01); *A61B 17/0231* (2013.01); *A61B 2017/00862* (2013.01); *A61B 2017/00907* (2013.01); *A61B 2090/306* (2016.02); *A61B 2090/309* (2016.02)

(58) Field of Classification Search
CPC ....... A61B 3/0008; A61B 3/12; A61B 5/0053; A61B 17/0231
See application file for complete search history.

(56) References Cited

U.S. PATENT DOCUMENTS

2012/0050683  A1*   3/2012  Yates ................... H04N 5/2251
                                                                         351/219

* cited by examiner

*Primary Examiner* — Anne M Hines
(74) *Attorney, Agent, or Firm* — Norris McLaughlin, P.A.

(57) ABSTRACT

An ophthalmic device for fundus examination comprising at least one light-permeable end, designed to come in contact with the eye and provided with a light source that allows illumination of the eye fundus cavity through the eyeball without the need of an external light source that may cause reflections or artifacts displayed on lenses or magnifying glasses used by professionals during the examination.

10 Claims, 4 Drawing Sheets

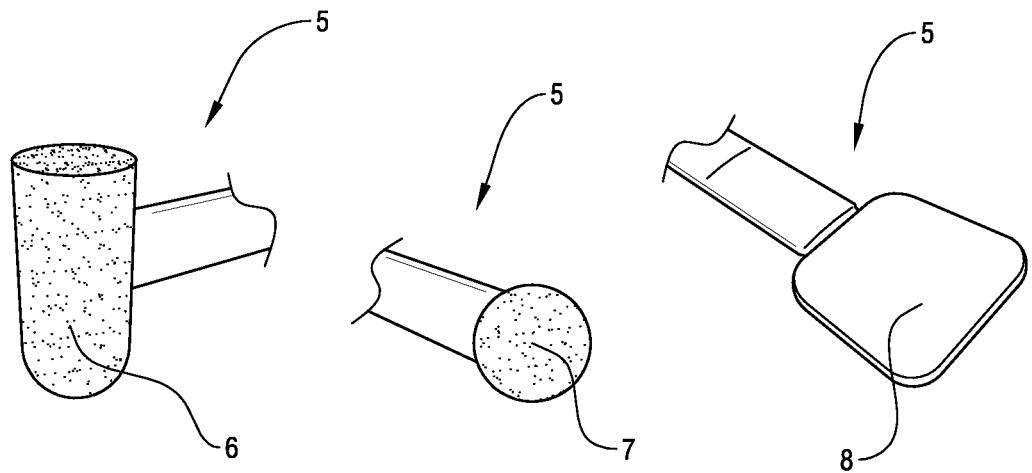
Fig. 3 Prior Art
Fig. 4 Prior Art
Fig. 5 Prior Art
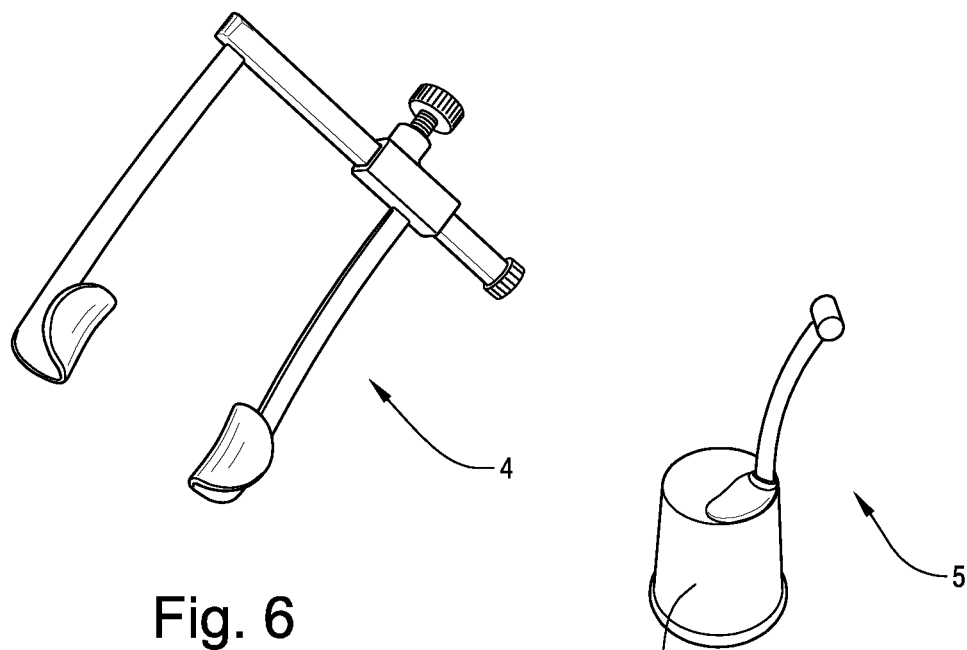
Fig. 6 Prior Art
Fig. 7 Prior Art

OPTHALMIC DEVICE FOR FUNDUS EXAMINATION

BACKGROUND OF THE INVENTION

Field of the Invention

The present invention relates to the field of devices, apparatuses and arrangements used in ophthalmology, preferably to carry out the fundus examination, and more particularly relates to a device that allows a direct illumination of the fundus cavity through of the eyeball in order to improve the processes in the fundus examination without presenting reflections or artifacts on the magnifying glasses used by professionals. Even though in the present description, reference is made to an ophthalmic device for fundus examination, it should be clear that the present invention can be adapted to be considered and used in any type of physical examination in which an area of the body has to be illuminated to examine it more accurately.

Description of the Prior Art

The fundus examination is well known in the field of art and it is known that it is one of the techniques that are usually performed during a complete ophthalmological examination. Fundus examination involves careful observation of the areas in the back of the eyeball, such as the retina, the macula, the blood vessels, the optic disk and the choroid.

The examination of the fundus is very important to detect certain serious pathologies in its initial phases. You can see diseases such as diabetic retinopathy, DMAE (age-related macular degeneration), macular degeneration or eye melanoma, among others. These types of examinations are usually included in a complete ophthalmological review, but in the case of diseases such as diabetes, premature retinopathy, eye infections and inflammations (posterior uveitis), high blood pressure or any alteration of the blood vessels, it is essential to study the eyeball fundus to check if there are damages in this area and to be able to establish appropriate treatments, in case any pathology is detected.

It can be said that the eyeball cavity is a dark chamber and therefore, it shall be illuminated to be able to visualize the structures: retina and its components (its layers, blood vessels), optic nerve, the interior vitreous gel and the outermost layers of the retina (choroid and sclera) in some situations. Currently, the fundus is performed by two lighting systems of that dark chamber (the eye fundus): illumination through the pupil, where the light passes through the dilated pupil, usually coaxially to the displays (ophthalmoscopes, microscopes). Any type of light (light, scanning laser, etc.); endoocular illumination, wherein light enters through the wall of the eyeball which is perforated during a surgical procedure, and optical fibers enter through probes. Used for vitrectomy; and ocular trans-illumination, used in few cases, to diagnose ocular tumors, when it is not evaluated by fundus examination (very anterior and peripheral lesions)

Within these trans-illuminations, trans-palpebral illumination has been described in which the skin of the eyelid is contacted with a powerful light source, which traverses: eyelid wall (skin, tarsal and conjunctiva), then eyeball wall (conjunctiva, sclera, colloids and retina) arriving by diffusion to illuminate the fundus. In very peripheral fundus lesions, an eyelid separator should be used (especially in premature babies and babies) and the eyeball should be rotated with an indenter or rotator. With the rotator, the eye is rotated through the twelve-hour positions of the fundus, making a full turn during the examination.

When you need to see a peripheral lesion or bring a part of the retina to the back and see that part or lesion through the pupil, both the eyelid separator and the indenter or rotator, are introduced below the eyelids, the first one to separate them and the second one to direct it towards the bottom of the conjunctiva sac and thus rotate the eye. When passing behind the eyelid, they directly contact the bulbar conjunctiva (membrane that covers the eyeball).

For all lighting methods mentioned above, the professional uses biconvex magnifying glasses, usually aspherical. Depending on the area of the fundus of the eye that you want to check, these magnifying glasses has to be angled and inclined to be able to observe, for example, the peripheral areas. This causes the coaxial light to reflect and produce reflections or artifacts caused by the rebound of light due to a reflection phenomenon, which are harmful during the examination.

By virtue of the above, it would be advisable to have a new arrangement, device or support that allows the fundus examination to be carried out without causing artifacts or reflections on the magnifying glasses used during the examination.

SUMMARY OF THE INVENTION

It is an object of the present invention to provide a new ophthalmic device for fundus examination that allows the illumination of the interior of the eyeball without the need of an external source of illumination that can cause artifacts or reflections visualized in the magnifying element (lens/magnifying glass) used by professionals during the examination.

It is still another object of the present invention to provide an ophthalmic device for fundus examination that prevents illumination through the thickness of the eyelid.

It is still another object of the present invention to provide an ophthalmic device for fundus examination that allows direct illumination through the inside of the eyeball simultaneously with its rotation.

It is another object of the present invention to provide an ophthalmic device for fundus examination that makes it possible to carry out it in a practical, fast and easy way.

It is further another object of the present invention to provide an ophthalmic device for fundus examination of the type used for the rotation of the eyeball and/or the opening of the eyelids comprising at least one first translucent end that is in operative contact with the eyeball, and at least one light source provided inside the device and which extends at least up to said first translucent end.

BRIEF DESCRIPTION OF THE DRAWINGS

For greater clarity and understanding of the object of the present invention, it has been illustrated in several figures, in which the invention has been represented in a preferred embodiment, all by way of example, wherein:

FIG. 3 shows one end of the known device of FIG. 3;

FIG. 4 shows another end of the device of FIG. 3;

FIG. 5 shows a perspective view of one end of a flat indenter of the prior art;

FIG. 6 shows a perspective view of a blepharostat according to prior art

FIG. 7 shows a perspective view of a "thimble" indenter according to the prior art;

DETAILED DESCRIPTION OF THE INVENTION

Referring now to the figures it is seen that the invention consists of a new ophthalmic device that allows direct illumination of the eyeball and in turn, its rotation, without this producing reflections or artifacts on the magnifying glasses used by professionals when they examine the eye. However, in order to provide a better understanding of the object of the present invention, conventional devices used in the field of eye examinations, particularly fundus examination, shall be described first. However, it should be noted that the teachings of the present invention can be applied to any medical instrument that has a part to be leant on the human body to examine an area thereof and it is necessary to have illumination through said body part.

Figure 1:
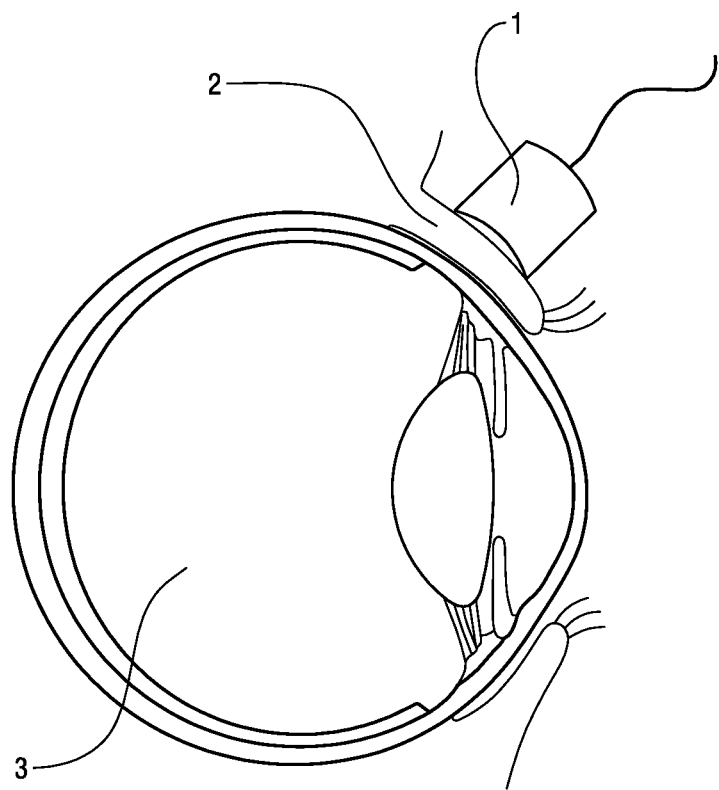
FIG. 1 shows a sectional side view of a trans-palpebral illumination method according to the prior art.
Figure 2:
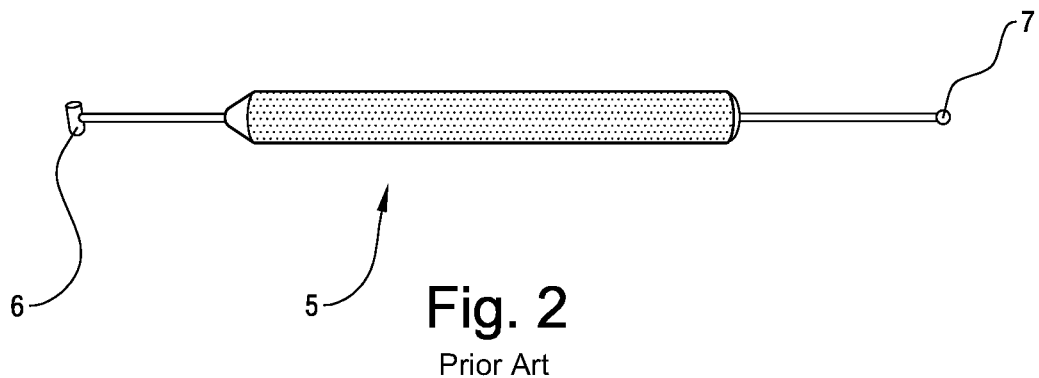
FIG. 2 shows a side view of an examination instrument known as a double ended indenter/rotator, according to the prior art.

According to FIG. 1 related to the prior art, a method of illumination of the eyeball known as "transpupillary illumination" can be observed, which consists in directing a bright coaxial light, such as that of an ophthalmoscope 1 through the eyelid 2 of the patient to illuminate the eyeball 3.

When the light hits the eyelid, we proceed to look for any obstruction to the light reflection. Opacity near the axis of the pupil usually appears as a dark shadow against the pupillary plane of the normal red reflex. The opacity must be located by asking the patient to look slowly upwards or downwards, or by changing the direction of light. Movements of the eye according to their relative position with respect to the pupillary plane change with the eye movements according to the pupillary plane.

There are also other methods such as endo-ocular illumination wherein light enters through the wall of the eyeball, perforated during a surgical procedure, and optical fibers enter through probes, being used for vitrectomy. As well as, there exists the ocular trans-illumination method used in few cases, to diagnose ocular tumors, when it is not possible to evaluate very anterior and peripheral lesions by fundus examination of the eye. Within the types of trans-illumination, it has been described that the trans-palpebral illumination, where the eyelid skin is contacted with a powerful light source, goes through the eyelid wall (skin, tarsal part and conjunctiva), then the eyeball wall (conjunctiva, sclera, colloids and retina) illuminating by diffusion the fundus.

It should be noted that, for all illumination methods, biconvex magnifying glasses, usually aspheric, are used. In this way, depending on the area of the fundus of the eye that you want to check, these magnifying glasses has to be angled and inclined to be able to observe, for example, the peripheral areas. However, this causes the coaxial light to reflect and produce reflections or artifacts due to the rebound of light by a reflection phenomenon. In all cases, these methods and illumination devices are only used to illuminate and have no other capacity, for example to rotate or indent the eyeball. In other words, they do not make it possible to act on the eye but only by providing illumination.

Medical devices used to act on the eyeball in ophthalmic examinations are varied. For example, in very peripheral fundus lesions, FIG. 6 of the prior art, a separator of eyelids or blepharostat 4 should be used, especially in premature babies and babies, and the eyeball has to be rotated with an indenter or rotator 5 such as the one illustrated in FIGS. 2 to 5 and 7 related to prior art. With one of the ends of the rotator 4 the eye is rotated through the twelve-hour positions of the fundus, making the full turn in the examination. When you need to see a peripheral lesion or bring a part of the retina to the back and see that part or lesion through the pupil, both the eyelid separator and the indenter or rotator, are introduced below the eyelids, the first one to separate them and the second one to direct it towards the bottom of the conjunctiva sac and thus rotate the eye. When passing behind the eyelid, they directly contact the bulbar conjunctiva (membrane that covers the eyeball).

It is highlighted that the indenter or rotator 5 can comprise respective ends having cylindrical shape 6 (FIG. 3 of the prior art), spherical shape 7 (FIG. 4 of the previous art), in the form of a "blade" 8 (FIG. 5 of the previous art), or in the form of a "thimble" 9 (figure of the previous art). In all cases, these ends allow rotation of the eyeball for a better examination of it. On the other hand, the blepharostat 4 allows keeping the eyelids open in order to expose the eyeball, the blepharostat is well known in the field of the art and for such reasons, descriptive details about it shall not be included.

As mentioned above, transpupillary illumination has the drawbacks of generating reflections or artifacts on the magnifying glasses used by professionals to perform the fundus examination. These reflections or artifacts obstruct the normal development of the examination and evaluation of the eyeball being a great trouble. As a result of the above, the present invention aims to solve these drawbacks by using a light source that strikes directly into the eye fundus cavity through the walls of the eyeball, thus avoiding the thickness of the eyelid that makes that light strength be lost and taking advantage of the maneuver of separating the eyelids and rotating or indenting the eyeball.

It is emphasized that reference numbers from 100 shall be used to indicate those parts and components of the present invention. Thus, and according to FIGS. 8 to 13, the ophthalmic device for fundus examination of the present invention is indicated by the general reference 101 and may comprise both a blepharostat, FIG. 11, and an indenter/rotator 102. Wherein, said indenter-rotator 102 comprises at least one translucent end 103 which may have a somewhat cylindrical body 104 (FIG. 8), with a sphere shape 105 (FIGS. 9 and 12) or flat or "blade" shape 106 (FIG. 10 or 13). The translucent end 103 comprises a solid body which may be made of a flexible, semi-flexible, rigid material, or a combination thereof. Likewise, it can be made of a polymeric, acrylic material, any material with similar characteristics that is biocompatible, or a combination thereof, and that is transparent or translucent.

The use of a translucent polymeric material, illustrated in dashed lines for a better understanding of the invention, allows in the first instance a better adaptation of the end of the indenter or rotator with the eyeball in order to avoid damage to it, and in the second instance, to allow the projection of the light beam of a light source 107. The ends 103, 104, 105 of the examination devices are illustrated in dashed lines or phantom lines, with the intention of making it clear that at least said ends of the examination device, according to the invention, are permeable to the light, for example transparent or translucent, to let out any light emitted from its interior or from any part thereof in order to illuminate the eyeball.

Figure 8:
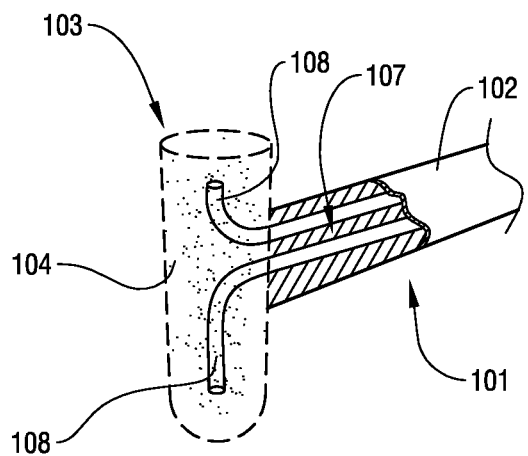
FIG. 8 shows a transluminal end according to the present invention, of a double-ended indenter/rotator examination instrument, for example, as illustrated in FIG. 2.
Figure 9:
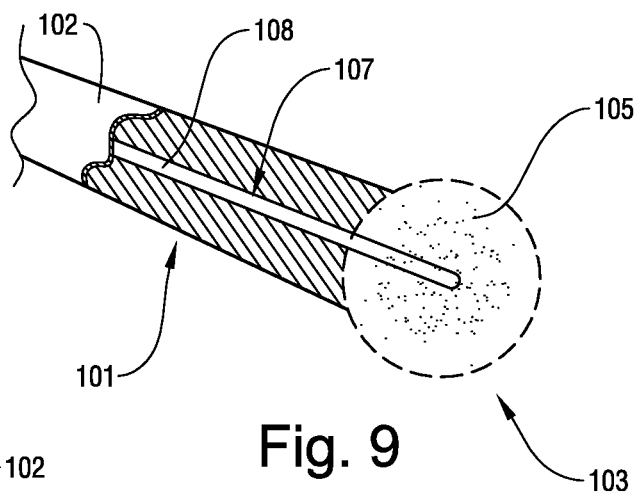
FIG. 9 shows another transluminal end according to the present invention, of a double ended indenter/rotator examination instrument.
Figure 10:
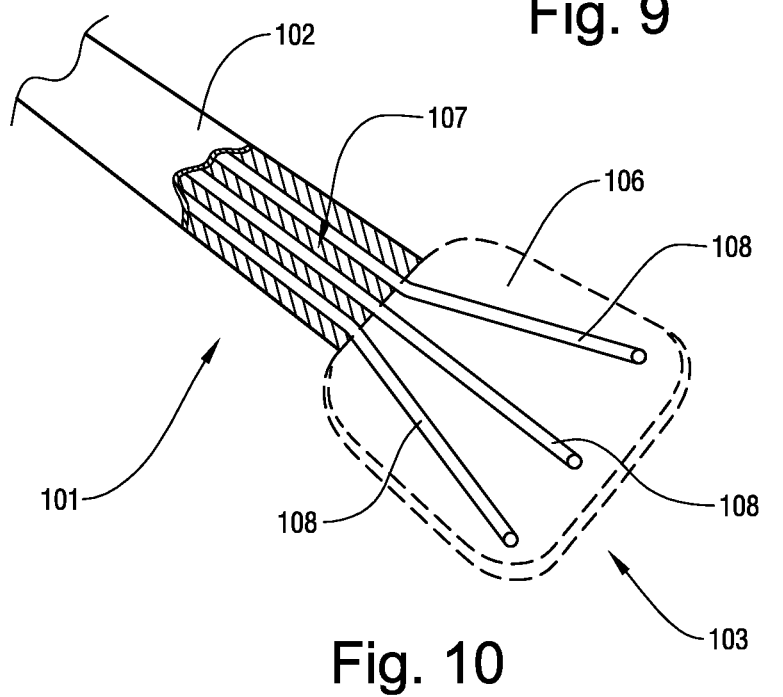
FIG. 10 shows a transluminal end according to the present invention, of a flat indenting instrument.

According to one of the objects of the present invention, the light source 107 is provided inside the indenter, or the blepharostat, and extends towards said translucent end 103, as illustrated in FIGS. 8 to 10. The light source 107 can be selected from the group consisting of optical fiber, LED, laser or a combination thereof. Although, the figure illustrates the use of optical fibers 108, this does not imply that the invention is limited to them, other forms of lighting being considered and used that can be integrated into the indenters, rotators or blepharostats without any inconvenience.

If optical fiber is used, as shown in FIGS. 8, 9, 10, the fibers 108 shall have their front end encapsulated within the transparent or translucent body 104, 105, 106, so that light is emitted by said ends with a opening angle that shall depend on the optical fiber used. The front end of the optical fiber can be oriented as desired to make the best use of its light cone. On the other hand, the rear end of the optical fiber shall be connected to a known light source, such as an LED, halogen light, etc. The supply of said light can be done by means of a battery or other known power supply.

Likewise, the light source 107 may be connected to a portable power supply (not shown) with rheostat intensity regulation (not illustrated), which are well known in the art and for such reasons, it is understood that his illustration or description is not necessary. Although one of the ends of the indenter 102 has been illustrated, this does not imply that the invention is limited to said configuration, but that the indenter may have at least two ends, both provided with the light source. In turn, the arrangement and quantity of optical fibers illustrated in FIGS. 8 to 10, is not a limitation for the invention, since they can vary in their arrangement and quantity for a better illumination of the fundus cavity.

Figure 11:
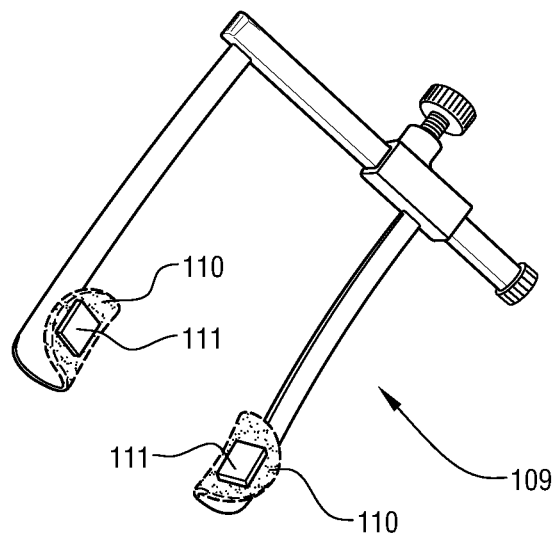
FIG. 11 shows the ends of a blepharostat including the transluminal characteristics of the present invention.

According to an alternative embodiment of the invention, illustrated in FIG. 11, the blepharostat 109 can also be provided with a light source at each end of its arms for opening the eyelids in order to further improve the illumination of the fundus cavity. Thus, the ends 110 intended to hold the eyelids open, may be made of any transparent or translucent material and contain encapsulated within the same respective light sources, for example optical fibers or LEDs 111. These LEDs shall be powered by a known electric power supply. Thus, when the professional enters the end of the indenter or rotator inside the eye, the LEDs 111 are responsible for illuminating the cavity through the walls of the eyeball, avoiding any type of reflection or artifact that can be seen on the magnifying glass used for the examination of the eye as occurs with the conventional devices and methods of the prior art.

Figure 12:
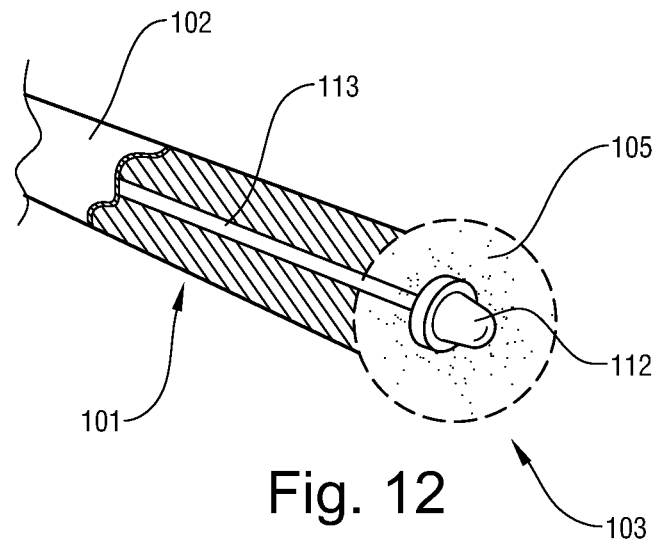
FIG. 12 shows a transluminal end according to an alternative of the present invention, of a double ended indenter/rotator examination instrument.
Figure 13:
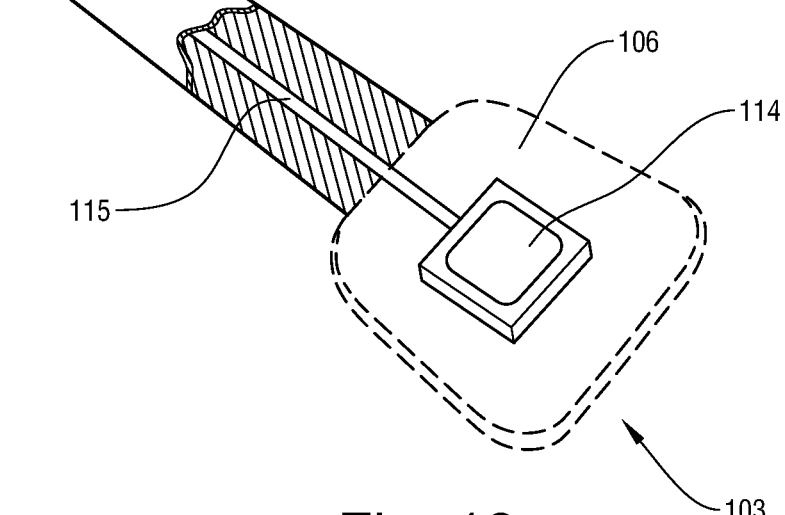
FIG. 13 shows another transluminal end according to an alternative of the present invention, of a double ended indenter/rotator examination instrument.

According to another embodiment of the invention, illustrated in FIG. 12, the spherical, translucent or transparent body 105 of an indenter-rotator may include one or more light sources such as, for example, a LED 112 that can receive electrical power through of a conductor 113.

Still in accordance with another embodiment of the invention, illustrated in FIG. 13, the spherical, translucent or transparent body 106 of a planar indenter may include one or more light sources such as an LED 114 that may be connected to a power source by means of a conductor 115.

In all embodiments that LEDs are used, these may be of any known type and the limitation of their use shall be defined by the necessary size of translucent or transparent bodies of rotators and/or indenters. For example, if these bodies are very small, Chip LEDs can be used, which are small and flat. For example, there are very small LEDS such as LEDs encapsulated in plastic and/or polymeric materials. There exist known LEDS bearing CSP (Chip Scale Package) technology, commercially available in Samsung Firm. There are also, from the same firm and technology, FEC LEDs (Fillet-Enhanced Chip-Scale Package). All of these LEDs can be used in the present invention.

In all cases of the invention, the ends and end bodies 103, 104, 105, 106 and 110 are ends and bodies that are designed and configured to come into contact with the eye or part of the eyeball, to bear against it, tighten it, rotate it, move it, that is, they have an operative purpose on the eyeball and at the same time they provide light that falls directly on the eyeball and towards the inside.

In this way, the ophthalmic device of the present invention is constituted and constructed, which thanks to the translucent end of a material, which can be polymeric, in combination with the light source, make it possible to optimize lighting and improve artifacts that produce the magnifying glasses since the light shall not hit the surface of the magnifying glass because it shall be housed inside the eye. By means of the invention, light is transmitted through the walls of the eyeball into the cavity of the fundus of the eye. In this way, it is illuminated from inside (retina and vitreous, and anterior internal structures of the eye, such as the ciliary body).

It is clarified that, the object of the present invention can be adapted and used in any type of blepharostat, indenter, rotator, as well as, can be considered, adapted and used in other areas of medicine in which a dark area difficult to access has to be illuminated to provide a better development of the respective examination.

We claim:

1. An ophthalmic device for fundus examination, the device comprising:
   at least a first light-permeable end that is designed and configured to come into operative contact with the eyeball to rotate and indent the eyeball, and
   at least one light source provided inside the device and extending at least up to said first light-permeable end,
   wherein the at least first light-permeable end is made of a light-permeable material and the at least one light source is encapsulated into the light-permeable material.

2. The ophthalmic device according to claim 1, wherein said light-permeable material is flexible, semi-flexible, rigid material, or a combination thereof.

3. The ophthalmic device according to claim 1, wherein said light-permeable material is a polymeric, acrylic material, any biocompatible material or a combination thereof.

4. The ophthalmic device according to claim 1, wherein said at least a first light-permeable end comprises at least two light-permeable ends that are in operative contact with the eyeball.

5. The ophthalmic device according to claim 1, wherein said light source is an optical fiber.

6. The ophthalmic device according to claim 1, wherein said light source is at least a LED.

7. The ophthalmic device according to claim 1, wherein said light source is at least a laser.

8. The ophthalmic device according to claim 1, wherein the device is selected from the group consisting of ocular indenters, rotators, blepharostats, or a combination thereof.

9. The ophthalmic device according to claim 1, wherein said permeable light-end is translucent.

10. The ophthalmic device according to claim 1, wherein said permeable light-end is transparent.

* * * * *